(12) United States Patent
Thuret-Hindges et al.

(10) Patent No.: US 11,747,347 B2
(45) Date of Patent: Sep. 5, 2023

(54) ASSAY FOR DIAGNOSING ALZHEIMER'S DISEASE

(71) Applicant: King's College London, Greater London (GB)

(72) Inventors: Sandrine Thuret-Hindges, London (GB); Simon Lovestone, London (GB); Jack Price, London (GB); Aleksandra Maruszak, London (GB); Tytus Murphy, London (GB)

(73) Assignee: King's College London, Greater London (GB)

( * ) Notice: Subject to any disclaimer, the term of this patent is extended or adjusted under 35 U.S.C. 154(b) by 368 days.

(21) Appl. No.: 16/335,812

(22) PCT Filed: Sep. 28, 2017

(86) PCT No.: PCT/GB2017/052904
§ 371 (c)(1),
(2) Date: Mar. 22, 2019

(87) PCT Pub. No.: WO2018/060709
PCT Pub. Date: Apr. 5, 2018

(65) Prior Publication Data
US 2019/0227083 A1 Jul. 25, 2019

(30) Foreign Application Priority Data
Sep. 30, 2016 (GB) .................................. 1616691

(51) Int. Cl.
*C12N 5/00* (2006.01)
*G01N 33/68* (2006.01)
*G01N 33/50* (2006.01)

(52) U.S. Cl.
CPC ..... *G01N 33/6896* (2013.01); *G01N 33/5058* (2013.01); *G01N 2510/00* (2013.01); *G01N 2800/2821* (2013.01); *G01N 2800/50* (2013.01); *G01N 2800/56* (2013.01)

(58) Field of Classification Search
None
See application file for complete search history.

(56) References Cited

U.S. PATENT DOCUMENTS

| | | | | |
|---|---|---|---|---|
| 2003/0073887 A1* | 4/2003 | Iliff | ........................ | G16H 50/20 600/300 |
| 2005/0037495 A1* | 2/2005 | Sah | ........................ | A61P 25/00 435/455 |

FOREIGN PATENT DOCUMENTS

WO    WO 2012/145363    10/2012

OTHER PUBLICATIONS

Anacker et al, Mo Psychiat 16: 738-750, 2011.*
Kyllonen et al Stem Cell Res Ther 4: 1-15, 2013.*
Borsini et al, Abstracts/Brain, Behav Immunity 57, Abstract#1744, p. e11, Oct. 2016.*
PNIRS 2016 Program, pp. 1-2, Jun. 8-11, 2016, (Borsini et al Abstract 1744—highlighted, p. 2).*
Grimes et al (Lancet 365: 1500-1505, 2005).*
Anacker et al, Mol Psychiat (Supp Mat) 16: 1-29, 2011.*
Jung-Testas et al (Exp Clin Endocrinol 86: 151-64, 1985—abstract).*
Foradori et al (Neurosc 149: 155-164, 2007).*
Maruszak et al bioRxiv (preprint server for biology), pp. 1-48, posted Aug. 13, 2017.*
Louneva et al., Caspase-3 is enriched in postsynaptic densities and increased in Alzheimer's disease. American Journal of Pathology, American Society for Investigative Pathology, US, vol. 173, No. 5, Nov. 1, 2008, pp. 1488-1495.
Płóciennik et al., Activated Caspase-3 and Nerodegeneration and Synaptic Plasticity in Alzheimer's Disease, Advances in Alzheimer's Disease, vol. 04, No. 3, Jan. 1, 2015, pp. 63-77.
International Search Report and Written Opinion for PCT/GB2017/052904 dated Nov. 24, 2017 in 13 pages.
Lazarov et al., "Neurogenesis and Alzheimer's disease: At the crossroads," Exp. Neurol., Jun. 2010, 223(2):267-281.
Nakayama, Motoshi, Office Action, Application No. 2019-517780, Japan Patent Office, dated Jul. 26, 2021.

* cited by examiner

*Primary Examiner* — Daniel E Kolker
*Assistant Examiner* — Aditi Dutt
(74) *Attorney, Agent, or Firm* — Gavrilovich, Dodd & Lindsey LLP (57) ABSTRACT

The invention disclosed herein is for an in vitro cell-based assay for predicting the conversion from mild cognitive impairment to Alzheimer's disease in a patient who has received a diagnosis of MCI. The method comprises the following steps: a) culturing human hippocampal progenitor cells in a culture medium comprising serum, obtained from said patient, during a period of proliferation of said progenitor cells; b) subsequently culturing said hippocampal progenitor cells in a culture medium comprising serum, obtained from said patient, during a period of differentiation of said progenitor cells; c) determining the level of proliferation of said cultured progenitor cells; d) determining the average cell count of said cultured progenitor cells; and e) monitoring apoptotic cell death after differentiation of the proliferated hippocampal progenitor cells, wherein the outcomes of each of (c) to (e) are applied to a statistical analysis, the result of which is predictive of conversion from MCI to AD in the patient.

19 Claims, 4 Drawing Sheets

ASSAY FOR DIAGNOSING ALZHEIMER'S DISEASE

This application is the U.S. National Stage under 35 U.S.C. § 371 of PCT App. No. PCT/GB2017/052904 filed on Sep. 28, 2017, which in turn claims the benefit of GB Patent App. No. 1616691.0 filed on Sep. 30, 2016. Each of the foregoing applications is hereby incorporated by reference in their entireties.

FIELD OF THE INVENTION

This invention relates to an assay for predicting conversion from mild cognitive impairment to Alzheimer's disease.

BACKGROUND OF THE INVENTION

Alzheimer's disease (AD) is the most common cause of dementia worldwide, currently afflicting an estimated 40 million people. Although AD can be hereditary, the majority of cases are sporadic, with life-style factors such as diet, exercise, and education all thought to contribute to the risk of developing late-onset AD. Due to the increase in age and sedentary living within the global population, the number of people with dementia is set to increase to 75 million by 2030, costing the global economy an estimated 2 trillion dollars in palliative care. This huge economic and emotional burden is partly due to our inability to both halt disease progression and diagnose AD pre-symptomatically.

Dementia due to AD is preceded by a long preclinical stage, followed by diagnosis of mild cognitive impairment (MCI). Importantly, not everyone diagnosed with MCI will eventually develop AD. Some will remain cognitively stable or progress to other diseases such as Lewy body dementia, vascular dementia and/or frontotemporal dementia.

The hippocampus is the most effected brain region in AD, with hippocampal neurons the main neuronal subtype whose degeneration is observed. As late onset AD cannot currently be diagnosed pre-symptomatically, by the time a patient is identified as suffering from AD, the hippocampus is often already considerably damaged. This compounds the difficulty in developing effective therapies, as treatments are required to be curative, as opposed to preventative. Furthermore, because of the progressive nature of cognitive decline observed in patients with AD, clinical trials often incorporate patients who are diagnosed with MCI, but may not necessarily go on to develop AD. The inclusion of these patients in clinical trials significantly impacts the ability to evaluate the efficacy of the therapy under investigation with any degree of certainty.

Another potential pathological feature of AD is the dysfunction of hippocampal neurogenesis (HN). HN is the process by which hippocampal neurons are continually generated in the brain. Until recently, it was unclear whether HN took place in the adult brain. However mounting evidence now suggests that HN plays a fundamental role in hippocampal-dependent learning and memory. HN is thought to be affected by blood-borne factors that can undergo dynamic exchange with the cerebrospinal fluid. These factors are collectively known as the systemic milieu (SM). The composition of the SM is greatly influenced by many of the same lifestyle factors that are known to be risk factors for AD. As such, dysfunction of HN, in addition to the degeneration of hippocampal neurons, may be a relevant pathological event in the progression of neurodegenerative diseases such as AD, especially as the hippocampus is one of the first affected brain structures in AD.

Nevertheless, the role of HN in the human brain and its clinical relevance remain unclear, predominantly because there is no means to directly measure HN or trace the fate of hippocampal progenitors in living individuals. It also remains unclear if changes in HN play a role in disease progression, or whether HN has a compensatory role to on-going pathology to provide cognitive resilience.

There is a need for the relationship between HN and the development of AD to be better understood, to enable the development of new clinical and diagnostic tools.

SUMMARY OF THE INVENTION

A first aspect of the invention provides an in vitro cell-based assay for predicting conversion from mild cognitive impairment (MCI) to Alzheimer's disease (AD) in an patient who has received a diagnosis of MCI, the assay comprising the steps of: (a) culturing human hippocampal progenitor cells in a culture medium comprising serum, obtained from said patient, during a period of proliferation of said progenitor cells; (b) subsequently culturing said hippocampal progenitor cells in a culture medium comprising serum, obtained from said patient, during a period of differentiation of said progenitor cells; (c) determining the level of proliferation of said cultured progenitor cells; (d) determining the average cell count of said cultured progenitor cells; and (e) monitoring apoptotic cell death after differentiation of the proliferated hippocampal progenitor cells, wherein the outcomes of each of (c) to (e) are applied to a statistical analysis, the result of which is predictive of conversion from MCI to AD in the patient.

A second aspect of the invention provides an in vitro cell-based assay for aiding the stratification of patients who have received a diagnosis of MCI for suitability for inclusion in an AD drug clinical trial, the assay comprising the steps of: (a) culturing human hippocampal progenitor cells in a culture medium comprising serum, obtained from said patient, during a period of proliferation of said progenitor cells; (b) subsequently culturing said hippocampal progenitor cells in a culture medium comprising serum, obtained from said patient, during a period of differentiation of said progenitor cells; (c) determining the level of proliferation of said cultured progenitor cells; (d) determining the average cell count of said cultured progenitor cells; and (e) monitoring apoptotic cell death after differentiation of the proliferated hippocampal progenitor cells, wherein the outcome of each of (c) to (e) can be used to determine the patient's suitability for inclusion in said clinical trial.

A third aspect of the invention provides an in vitro cell-based assay for aiding the assessment of the efficacy of a therapy administered to a patient who has been diagnosed with MCI, comprising: (a) culturing human hippocampal progenitor cells in a culture medium comprising serum, obtained from said patient, during a period of proliferation of said progenitor cells; (b) subsequently culturing said hippocampal progenitor cells in a culture medium comprising serum, obtained from said patient, during a period of differentiation of said progenitor cells; (c) determining the level of proliferation of said cultured progenitor cells; (d) determining the average cell count of said cultured progenitor cells; and (e) monitoring apoptotic cell death after differentiation of the proliferated hippocampal progenitor cells, wherein the assay is repeated at regular intervals during the period of treatment to generate results for each of (c) to (e) at different time points, and wherein said results from different time points are compared to aid assessment of the efficacy of said therapy.

A fourth aspect of the invention provides an in vitro cell-based assay for monitoring disease progression in a patient who has been diagnosed with MCI, comprising: (a) culturing human hippocampal progenitor cells in a culture medium comprising serum, obtained from said patient, during a period of proliferation of said progenitor cells; (b) subsequently culturing said hippocampal progenitor cells in a culture medium comprising serum, obtained from said patient, during a period of differentiation of said progenitor cells; (c) determining the level of proliferation of said cultured progenitor cells; (d) determining the average cell count of said cultured progenitor cells; and (e) monitoring apoptotic cell death after differentiation of the proliferated hippocampal progenitor cells, wherein the method is repeated at regular intervals to generate results for each of at (c) to (e) different time points, and wherein said results from different time points are compared to monitor disease progression.

A fifth aspect of the invention is directed to the use of a substrate comprising human hippocampal progenitor cells in an assay or method according to any of the preceding aspects of the invention.

A sixth aspect of the invention is directed to the use of hippocampal neurogenesis as a biomarker for conversion from MCI to AD, a biomarker for AD progression and/or a biomarker for monitoring AD.

A seventh aspect of the invention is directed to the use of hippocampal neurogenesis as a target for treatment of AD and/or as a target for intervention to delay the onset of AD.

An eighth aspect of the invention is directed to the use of hippocampal neurogenesis as a biomarker for conversion from MCI to AD according to the sixth aspect of the invention, or as a target for treatment of AD and/or as a target for intervention to delay the onset of AD according to the seventh aspect of the invention, wherein hippocampal neurogenesis is measured in vitro by exposing immortalised human hippocampal progenitor cells to human serum, preferably to a final concentration of human serum of in the range of from 0.5 (v/v) % to 5 (v/v) %, most preferably to a final concentration of 1 (v/v) %.

DESCRIPTION OF THE DRAWINGS

The invention is described with reference to the following drawings, in which.

DETAILED DESCRIPTION OF THE INVENTION

This invention is based on the inventors' finding that serum samples obtained from patients with mild cognitive impairment (MCI) differentially affect hippocampal neurogenesis (HN) in vitro. More specifically, the inventors have discovered that the degree to which a patient's serum modulates HN is an accurate predictor of whether the patient will go on to develop Alzheimer's disease (AD). In particular, inventors have found that the degree to which a patient's serum modulates HN, in combination with lifestyle factors such as the individual's education attainment status and/or diet, are accurate predictors of whether the MCI patient will go on to develop AD.

On the basis of this finding, the present inventors have developed a rapid, non-invasive in vitro assay that enables the diagnosis of AD pre-symptomatically in patients with MCI. This can be achieved by supplementing cell culture medium with a small sample of serum obtained from a patient and using said medium to culture human hippocampal progenitor cells in vitro. As the cells undergo a period of proliferation and differentiation, different biological phenomena can be measured and subsequently combined into a statistical analysis that can accurately predict whether a patient with MCI will develop AD. The ability to diagnose AD before the onset of symptoms provides an invaluable window for therapeutic intervention in order to prevent further, or even reverse, cognitive decline.

Accordingly, a first aspect of the invention provides an in vitro cell-based assay for predicting conversion from mild cognitive impairment (MCI) to Alzheimer's disease (AD) in a patient who has received a diagnosis of MCI, wherein the assay comprises the steps of:

(a) culturing human hippocampal progenitor cells in a culture medium comprising serum, obtained from said patient, during a period of proliferation of said progenitor cells;

(b) subsequently culturing said hippocampal progenitor cells in a culture medium comprising serum, obtained from said patient, during a period of differentiation of said progenitor cells;

(c) determining the level of proliferation of said cultured progenitor cells;

(d) determining the average cell count of said cultured progenitor cells; and (e) monitoring apoptotic cell death after differentiation of the proliferated hippocampal progenitor cells, wherein the outcomes of each of (c) to (e) are applied to a statistical analysis, the result of which is predictive of conversion from MCI to AD in the patient.

The terms "serum" and "systemic milieu (SM)" are used interchangeably herein and have their usual meaning in the art. Serum is a component of blood that is neither a blood cell nor a clotting factor. Serum is blood plasma excluding the fibrinogens.

The composition of the systemic milieu is greatly affected by numerous factors including diet, exercise, and inflammatory status. The systemic milieu may be able to affect processes disrupted in AD and other neurodegenerative diseases, such as human neurogenesis.

Serum (or the SM) can be extracted from a sample of blood obtained from a patient, preferably a human patient, using standard phlebotomy techniques that are well known in the art and conventional and routine to the skilled practitioner. In the context of the present invention, the SM comprises only the serum component of the blood sample.

As used herein, the term "hippocampal neurogenesis (HN)" refers to the process by which new neurons are created in the dentate gyrus of the hippocampal brain region. HN is most active during pre-natal development and is responsible for populating the growing brain, where neural progenitor cells undergo differentiation into mature neurons. Neurogenesis can also take place in the sub-ventricular zone, where new neurons can migrate to the olfactory bulb via the rostral migratory stream. It is stimulated in the presence of various growth factors and mitogens. The precise combination of growth factors determines the type of neuron that is generated.

The term "hippocampal progenitor cell" has its usual meaning in the art, and refers to progenitor cells involved in neurogenesis in the hippocampal region of the brain. In a preferred embodiment of the present invention, the hippocampal progenitor cells are human multipotent hippocampal progenitor cells.

The term "mild cognitive impairment (MCI)" has its usual meaning in the art and refers to a brain function syndrome involving the onset of a decline in cognitive function beyond that which is typically expected based on the age and education of an individual. MCI is not significant enough to interfere with the daily activities of the individual. It may occur as a transitional stage between normal aging and dementia-type diseases, such as Alzheimer's disease. MCI can, for example, be diagnosed according to the criteria defined in Petersen, R. C., et al., Arch Neurol. (1999) 56(3): p.303-8.

The term "Alzheimer's disease (AD)" has its usual meaning in the art and refers to a chronic neurodegenerative disease. AD can, for example, be diagnosed according to the criteria defined in McKhann, G. et al., Neurology (1984) 34(7): p.939-44.

The terms "subject" and "patient" are used interchangeably herein, and refer to an individual who has received a clinical diagnosis of MCI. The patient or subject may be any mammal, such as a monkey, pig, cat, dog or horse, but preferably the patient or subject is a human being.

The term "statistical analysis" refers to any method into which the results of the measured events of the assay can be inputted to provide an indication as to whether the patient will go on to develop a disease. In the context of this invention, the preferred output of the statistical analysis is a probability score that will indicate the likelihood of a patient with MCI converting to AD. Preferably, the probability score is related to the likelihood of the patient converting to AD within 3.5 years from diagnosis of MCI (time point zero).

Particularly suitable statistical analyses will be well known to the skilled statistician. The most suitable statistical analysis will be able to integrate the results from multiple measurable events of the assay. In a preferred embodiment of the invention the method of statistical analysis is logistic regression. Logistic regression is used widely in many fields, including medicine. For example, logistic regression analysis has been used to determine the severity (or probability) of a patient developing diabetes based on a number of variable factors (i.e. measurable events), including age, sex, body mass index, and the results of multiple blood tests. Logistic regression is a binary logistic model used to estimate a binary response based on one or more independent variables (i.e. measured variables). Therefore, based on the results of the combined measurable events, the probability of a patient developing a disease will be between 0 and 1. The results of the probability scores from a cohort of patients known to have or not have the disease can therefore be used to construct a logistic regression curve, where the probability of developing the disease is plotted versus the combined value of the independent variables (i.e. measured events). The resulting curve can then be fitted with a logistic regression curve. The linear regression curve (or function of the curve) can then be used to assess the probability of a patient developing the disease, based on the results of the independent variables (i.e. measured events), where the probability will be reported as any value between 0 and 1, where 0 indicates a 0% probability of developing the disease, and 1 indicates a 100% probability of the patient developing the disease. In this invention, the probability score reports of the likelihood of a patient with MCI converting to AD.

As a minimum, the statistical analysis will be able to integrate results of the level of proliferation observed after or during the proliferation phase, the average cell count after or during the proliferation phase, and the level of apoptosis observed after the differentiation phase. However multiple other measurable phenomena could also be included in the statistical analysis. For example, one or more of the number of glial cells, mature neurons, or immature neurons determined to be present after the differentiation or proliferation phases may also be included in the statistical analysis.

The measurable events may not be limited to events directly measureable from the assay. In a preferred embodiment of the invention, one or more of the patient's lifestyle factors are also included in the statistical analysis. Said lifestyle factors may include the education status of the patient, dietary factors, the patient's alcohol intake, whether the patient smokes or has ever smoked, and whether they live alone (solitary living). Education status is defined as the number of years of formal education received by the subject. Formal education is defined herein as years spent at school, college, university and years spent studying for post-graduate or higher level qualifications. Dietary factors include intake of supplements, in particular vitamins and omega-3 fatty acids.

The utility or validity of combining the results of (c) to (e) into a statistical analysis for determining the likelihood of a patient with MCI converting to AD can be visualised using a Receiver operating characteristic (ROC) curve. A ROC curve depicts a trade off in specificity and sensitivity of a diagnostic tool and expresses its accuracy. On the y-axis is sensitivity, or the true-positive fraction (i.e. the number of patients with MCI correctly identified as going on to develop AD by the assay) defined as [(number of true-positive test results)/(number of true-positive+number of false-negative test results)]. This has also been referred to as positivity in the presence of a disease or condition. It is calculated solely from the affected subgroup (i.e. patients who have converted to AD). On the x-axis is the false-positive fraction (i.e. patients with MCI incorrectly identified by the assay as converters to AD, or 1−specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC curve is independent of the prevalence of disease in the sample. Each point on the ROC curve represents a sensitivity/specificity pair corresponding to a particular decision threshold. A test with perfect discrimination (no overlap in the two distributions of results) has an ROC curve that passes through the upper left corner, where the true-positive fraction is 1.0, or 100% (perfect sensitivity), and the false-positive fraction is 0 (perfect specificity). The theoretical curve for a test with no discrimination (identical distributions of results for the two groups) is a 45° diagonal line from the lower left corner to the upper right corner. Most curves fall in between these two extremes. Qualitatively, the closer the curve is to the upper left corner, the higher the overall accuracy of the test.

One convenient goal to quantify the diagnostic accuracy of a laboratory test is to express its performance by a single number. The most common global measure is the area under the curve (AUC) of the ROC curve. The area under the ROC curve is a measure of the probability that the perceived measurement will allow correct identification of a condition. By convention, this area is always ≥0.5. Values range between 1.0 (perfect separation of the test values of the two groups) and 0.5 (no apparent distributional difference between the two groups of test values). The area does not depend only on a particular portion of the curve such as the point closest to the diagonal or the sensitivity at 90% specificity, but on the entire curve. This is a quantitative, descriptive expression of how close the ROC curve is to the perfect one (area=1.0). In the context of the present invention, the two different conditions are whether a patient with MCI will go on to develop AD or will not go on to develop AD. The ROC curve data and the clinical requirements of the test may be considered together when calculating a threshold or "cut-off" value to be used in future application of the diagnostic test. When the value is measured above (or below) this cut-off value, the test is considered "positive" and further action may be taken appropriate to the clinical condition. An important feature in setting the cut-off value is the required specificity of the test (i.e. the true positive rate). By convention, the required specificity for many diagnostic tests is stated in advance to be 90%, 95%, or as close to 100% as practical. For test that predicts conversion of MCI to AD, it is likely that an effective test will need to approach 100%, on account of the severe consequences of false negative results for patients. The cut-off value required to achieve these specificities may then be read from the ROC curve. This point on the curve will also denote a value for test sensitivity (true negative rate). Alternatively, the optimum cut-off value may be obtained by selecting the point on the ROC curve closest to the top-left corner of the graph. The AUC of this particular assay for diagnosing conversion to AD is 0.965 (FIG. 4) meaning that the probability score derived from the assay has a confidence value of 96.5%.

In order for the assay of the invention to be successfully performed, a range of serum concentrations can be added to the cell culture medium in steps (a) and (b). The optimum serum concentration to be used in the assay is a balance between using as little serum as possible while achieving a strong assay read-out. With this in mind, the inventors have found the optimal concentration range to be from 0.5 (v/v) % to 5 (v/v) % serum in the media. Thus, in a preferred embodiment, the final concentration of the serum in the culture medium in (a) and (b) is from 0.5 (v/v) % to 5 (v/v) %. Most preferably, the serum concentration is 1 (v/v) %.

In a preferred embodiment, step (a) comprises adding the serum to the culture medium 24 hours after seeding the cells in the culture medium. The culture medium in step (a) preferably comprises one or more of epidermal growth factor (EGF), basic fibroblast growth factor (bFGF) and 4-hydroxytestosterone (4-OHT). EGF, bFGF and 4-OHT are a combination of growth factors that allow the indefinite proliferation of human hippocampal progenitor cells. Preferably culture medium in step (a) comprises all three of these growth factors. The period of proliferation referred to in step (a) is preferably a 48 hour period.

In a preferred embodiment, the culture medium is changed between steps (a) and (b). Preferably, the culture medium used in step (b) does not comprise EGF, bFGF and 4-OHT. The removal of EGF, bFGF and 4-OHT from the cell culture medium induces the spontaneous differentiation of the progenitor cells into neurons, astrocytes, and oligodendrocytes. Preferably serum is added to the culture medium at the beginning of the differentiation period of step (b). The period of differentiation referred to in step (b) is preferably a period of up to 7 days.

In a preferred embodiment, the assay according to the first aspect of the invention comprises a further step of determining one or more of the patient's lifestyle factors. In a preferred embodiment, the education status of the patient is included in the statistical analysis. Preferably, the education status corresponds to the total number of years of formal education. Preferably, the education status of the patient is included in the statistical analysis in order to predict conversion of the patient from MCI to AD.

In a preferred embodiment the human hippocampal progenitor cells used in the assay of the invention are conditionally immortalised, for example by introducing the c-mycER$^{TAM}$ oncogene by retroviral transduction, so that the cells differentiate indefinitely in the presence of EGF, bFGF, and 4-OHT. More preferably, the hippocampal progenitor cells are cells from the HPC0A07 cell line, more preferably HPC0A07/03C cells. This cell line and the c-mycER$^{TAM}$ oncogene transduction system is described in detail in EP1645626 A1 (the contents of which are incorporated by reference in their entirety). HPC0A07 cells are deposited under the ECACC Accession number 04092302.

In a preferred embodiment, the level of proliferation of the hippocampal progenitor cells is determined at the end of the proliferation period. Proliferation can be quantified by measuring the levels of particular cellular markers known to be increased during proliferation. One such marker that can be measured to determine the level of proliferation is Ki67. Ki67 is a nuclear protein associated with ribosomal RNA synthesis. The level of Ki67 can be measured by a number of different methods, including by ELISA assay, ribosome profiling, flow cytometry, fluorescence microscopy, or Western blot analysis.

In a preferred embodiment Ki67 is the marker used for determining the level of proliferation. Ki67 expression can be measured using an anti-Ki67 antibody, wherein the antibody may be conjugated to a marker that enables its detection after binding to Ki67.

In a preferred embodiment, the average cell count is determined at the end of the proliferation period and at the end of the differentiation period. Techniques and methodologies for counting live or fixed cells are well known to the skilled person. By way of non-limiting example, the semi-automatic quantification method performed using the Cellinsight Personal Cell Imager (ThermoFisher Scientific) is particularly suitable for counting fixed cells. This method can be performed according to the manufacturer's instructions.

In a preferred embodiment, apoptotic cell death is determined at the end of the differentiation period. Apoptosis, or apoptotic cell death, is a finely controlled mechanism by which cells undergo programmed cell death. Apoptosis can be measured by detecting any one of a number of morphological changes that cells undergo during apoptosis. Such morphological changes include membrane blebbing, cell shrinkage, chromatin condensation and fragmentation, and global mRNA decay. By way of a non-limiting example, the number of apoptotic cells within a cell population can be determined using flow cytometry, due to the unique light scattering profile exhibited by apoptotic cells resulting from their condensed chromatin structure and shrunken cellular morphology. Common nuclear fluorescent markers can also be used to detect apoptosis, as the unique chromatin structure within apoptotic nuclei give rise to distinct fluorescent signatures of several nuclear stains. The unique metabolic profile of apoptotic cells means that tests that quantify the presence of certain metabolites, such as ADP and ATP, can also be used to measure apoptosis. Alternatively, fluorescence microscopy or Western blot analysis can be used to quantify the level proteins known to be upregulated during apoptosis. Suitable apoptotic-associated proteins will be well known to the skilled person, any of which are suitable for detecting and quantifying apoptosis in the context of this invention. Preferably, the level of cleaved caspase 3 (CC3) is used to quantify the degree of apoptosis. Preferably, the level of CC3 is measured using an anti-CC3 antibody.

It is envisaged that the evolution of the results of (c) to (e) over time could be used to indicate the progression of a patient having received a diagnosis of MCI towards AD over time. For example, the results of (c) to (e) could be applied to a statistical analysis in order to indicate a probability of the patient converting to AD at each time point. An increase in a probability score would indicate that the patient is further progressing towards converting to AD. A decrease in a probability score would indicate that the patient is not progressing further towards converting to AD. The evolution of a probability of conversion to AD could also be used to monitor the efficacy of a therapy for preventing conversion to AD. For example, if a probability score decreases or stays the same over time during administration of the therapy, the therapy is efficacious. Alternatively, if a probability score increases over time during administration of the therapy, then the therapy is not efficacious. Similarly, the results of (c) to (e) may be used to identify compounds that inhibit modulation of HN by a patient's serum, thus inferring that a particular compound may be a promising lead candidate for developing into a treatment for AD. By way of example, the serum obtained from a patient known to have converted from MCI to AD could be incubated in the presence and absence of candidate drug molecules to observe how the results or (c) to (e) are altered by the compound. The results of (c) to (e) in the presence of the compound could be applied to a statistical analysis to generate a probability and compared to a probability score calculated from the results of (c) to (e) in the absence of a compound. If a probability score for converting to AD is lower in the presence of the compound, then the drug may be considered a promising candidate molecule for developing into a therapeutic composition.

Therefore, a second aspect of the invention provides an in vitro cell-based assay for aiding the stratification of patients who have received a diagnosis of MCI for suitability for inclusion in an AD drug clinical trial. This assay comprises:

(a) culturing human hippocampal progenitor cells in a culture medium comprising serum, obtained from said patient, during a period of proliferation of said progenitor cells;

(b) subsequently culturing said hippocampal progenitor cells in a culture medium comprising serum, obtained from said patient, during a period of differentiation of said progenitor cells;

(c) determining the level of proliferation of said cultured progenitor cells;

(d) determining the average cell count of said cultured progenitor cells; and (e) monitoring apoptotic cell death after differentiation of the proliferated hippocampal progenitor cells, wherein the outcome of each of (c) to (e) are applied to a statistical analysis, the result of which can be used to determine the patient's suitability for inclusion in said clinical trial.

In a preferred embodiment of the second aspect of the invention, the method can be used to retrospectively determine whether patients who have been included in an AD drug clinical trial were suitable candidates for inclusion in said trial. Many failed clinical trials for AD therapies include patient cohorts which incorporate both patients suffering from MCI and patients suffering from AD. The therapies are typically administered to the whole MCI group, irrespective of whether the patient is likely to go on to develop AD. The inclusion of MCI patients with a low probability of developing AD in a clinical trial investigating the efficacy of an AD therapy is likely to diminish the effectiveness and reliability of the results of the trial. This assay can therefore be used to determine whether the therapy failed to reverse or inhibit cognitive decline because the patient did not go on to convert to AD. Inclusion of only patients who were suitable for inclusion in the trial in the analysis of the trial results will enable a more accurate picture of the therapeutic effect to emerge.

In a preferred embodiment, the assay further comprises measuring one or more of the following: (f) the level of mature neurons, immature neurons, or glial cells present after differentiation, or (g) the level of apoptosis during or after proliferation. The outcome of (f) and/or (g) can be used to determine the patient's suitability for inclusion in a clinical trial.

Preferably, the level of immature neurons, mature neurons, or glial cells is measured by detecting the level of expression of Dcx, Map2, or S100β, respectively. Preferably, the level of apoptosis is measured by detecting the level of expression of CC3. The level of expression of any of these proteins can be quantified using any of the conventional methods previously described.

A third aspect of the invention provides an in vitro cell-based assay for aiding the assessment of the efficacy of a therapy administered to a patient who has been diagnosed with MCI. The assay comprises the steps of:

(a) culturing human hippocampal progenitor cells in a culture medium comprising serum, obtained from said patient, during a period of proliferation of said progenitor cells;

(b) subsequently culturing said hippocampal progenitor cells in a culture medium comprising serum, obtained from said patient, during a period of differentiation of said progenitor cells;

(c) determining the level of proliferation of said cultured progenitor cells;

(d) determining the average cell count of said cultured progenitor cells; and (e) monitoring apoptotic cell death after differentiation of the proliferated hippocampal progenitor cells, wherein the assay is repeated at regular intervals during the period of treatment to generate results for each of (c) to (e) at different time points, and wherein said results from different time points are compared to aid assessment of the efficacy of said therapy.

In a preferred embodiment of the third aspect of the invention, the patient being administered the therapy is predicted to convert from MCI to AD. Preferably, the prediction of conversion from MCI to AD is the result of carrying out the assay according to the first aspect of this invention.

In this aspect of the invention, the therapy being administered to the patient is intended to prevent progression from MCI to AD.

In a preferred embodiment, said regular intervals are six-monthly intervals. Performing the assay at regular intervals allows the longitudinal efficacy of the therapy to be monitored. Preferably, intervals are calculated from a baseline ($T_0$) corresponding to the initial diagnosis of MCI.

In a preferred embodiment, the assay further comprises measuring one or more of the following: (f) the level of mature neurons, immature neurons, or glial cells present after differentiation, and/or (g) the level of apoptosis during or after proliferation. The outcome of (f) and/or (g) can be used to monitor the efficacy of a therapy over time.

Preferably, the level of immature neurons, mature neurons, or glial cells is measured by detecting the level of expression of Dcx, Map2, or S100β, respectively. Preferably the level of apoptosis is measured by detecting the level of expression of CC3. The level of expression of any of these proteins can be quantified using any of the conventional methods described herein.

According to a fourth aspect, the present invention provides an in vitro cell-based assay for monitoring disease progression in a patient who has been diagnosed with MCI. The assay comprises the steps of:

(a) culturing human hippocampal progenitor cells in a culture medium comprising serum, obtained from said patient, during a period of proliferation of said progenitor cells;

(b) subsequently culturing said hippocampal progenitor cells in a culture medium comprising serum, obtained from said patient, during a period of differentiation of said progenitor cells;

(c) determining the level of proliferation of said cultured progenitor cells;

(d) determining the average cell count of said cultured progenitor cells; and (e) monitoring apoptotic cell death after differentiation of the proliferated hippocampal progenitor cells, wherein the method is repeated at regular intervals to generate results for each of (c) to (e) at different time points, and wherein said results from different time points are compared to monitor disease progression.

In a preferred embodiment of the fourth aspect of the invention, said regular intervals are six-monthly intervals. Preferably, intervals are calculated from a baseline ($T_0$) corresponding to the initial diagnosis of MCI.

In another preferred embodiment, the assay further comprises measuring one or more of the following: (f) the level of mature neurons, immature neurons, or glial cells present after differentiation, and/or (g) the level of apoptosis during or after proliferation. The results for (f) and/or (g) can be compared at different time points to aid the monitoring of disease progression.

Preferably, the level of immature neurons, mature neurons, or glial cells is measured by detecting the level of expression of Dcx, Map2, or S100β, respectively. Preferably the level of apoptosis is measured by detecting the level of expression of CC3. The level of expression of any of these proteins can be quantified using any of the conventional methods described herein.

In preferred embodiments of each of the second, third and fourth aspects of the invention, the final concentration of the serum in the culture medium in steps (a) and (b) is from 0.5 (v/v) % to 5 (v/v) %, most preferably 1 (v/v) %.

In preferred embodiments of each of the second, third and fourth aspects of the invention, step (a) comprises adding the serum to the culture medium 24 hours after seeding the cells in the culture medium. Preferably, the culture medium in step (a) comprises EGF, bFGF and 4-OHT.

In preferred embodiments of each of the second, third and fourth aspects of the invention, the period of proliferation referred to in step (a) is a 48 hour period.

In preferred embodiments of each of the second, third and fourth aspects of the invention, the culture medium is changed between steps (a) and (b). Preferably the culture medium used in (b) does not comprise EGF, bFGF and 4-OHT. The serum may be added to the culture medium at the beginning of the differentiation period of step (b). Preferably, the period of differentiation referred to in step (b) is a period of up to 7 days.

In preferred embodiments of each of the second, third and fourth aspects of the invention, the assay comprise a further step of determining one or more of the patient's lifestyle factors. In a preferred embodiment the education status of the patient is included in the statistical analysis. Preferably, the education status corresponds to the total number of years of formal education.

In preferred embodiments of each of the second, third and fourth aspects of the invention, the hippocampal progenitor cells used in the assays are conditionally immortalised, for example by introducing the c-mycER oncogene by retroviral transduction, so that the cells differentiate indefinitely in the presence of EGF, bFGF, and 4-OHT. More preferably, the hippocampal progenitor cells are cells from the HPC0A07 cell line, more preferably HPC0A07/03C cells.

In preferred embodiment, the level of proliferation of the hippocampal progenitor cells is determined at the end of the proliferation period. Preferably, the level of proliferation is determined by measuring Ki67 expression of the hippocampal cells. Ki67 expression can be measured using an anti-Ki67 antibody.

In preferred embodiments of each of the second, third and fourth aspects of the invention, the average cell count is determined at the end of the proliferation period and at the end of the differentiation period.

In preferred embodiments of each of the second, third and fourth aspects of the invention, apoptotic cell death is determined at the end of the differentiation period. Apoptotic cell death can be determined by measuring CC3 expression. CC3 expression can be measured using an anti-CC3 antibody.

A fifth aspect of the invention is directed to the use of a substrate comprising human hippocampal progenitor cells in an assay according to any of the first to fourth aspects of the invention described above.

Preferably, the hippocampal progenitor cells used in the assays are conditionally immortalised, for example by introducing the c-mycER oncogene by retroviral transduction, so that the cells differentiate indefinitely in the presence of EGF, bFGF, and 4-OHT. More preferably, the hippocampal progenitor cells are cells from the HPC0A07 cell line, more preferably HPC0A07/03C cells.

The substrate may be any convention substrate for performing a cell-based assay. Suitable substrates will be apparent to the skilled person.

A sixth aspect of the invention is directed to the use of hippocampal neurogenesis as a biomarker for conversion from MCI to AD, a biomarker for AD progression and/or a biomarker for monitoring AD.

In a seventh aspect of the invention, there is provided the use of hippocampal neurogenesis as a target for treatment of AD and/or as a target for intervention to delay the onset of AD.

An eighth aspect of the invention is directed to the use of hippocampal neurogenesis as a biomarker for conversion from MCI to AD according to the sixth aspect of the invention, or as a target for treatment of AD, and/or as a target for intervention to delay the onset of AD according to the seventh aspect of the invention. Preferably, hippocampal neurogenesis is measured in vitro by exposing immortalised human hippocampal progenitor cells to human serum, preferably to a final concentration of human serum of 1 (v/v) %.

In a preferred embodiment, apoptotic cell death is determined at the end of the differentiation period.

The invention will now be described further with reference to the following non-limiting example.

Example

By utilising human hippocampal progenitor cells and longitudinal serum samples from MCI patients who either converted to AD (MCI converters) or remained cognitively stable over consecutive follow-up visits (MCI non-converters), the inventors sought to establish the contribution of human systemic environment (i.e. the composition of the systemic milieu) to HN and to determine if our HN assay could be used in predicting conversion from MCI to AD.

Materials and Methods

Cell line

All experiments were performed using the Multipotent Human Hippocampal Progenitor/Stem Cell Line HPC0A07/03C (ReNeuron Limited, UK), derived from the first trimester female foetal hippocampal tissue following normal termination and in accordance with UK and USA ethical and legal guidelines, and obtained from Advanced Bioscience Resources (Alameda Calif., USA) (Stangl, D. et al 2009; Zunszain, P. A. et al 2012; Anacker. C. et al 2013). HPC0A07/03C cells were conditionally immortalised by introducing c-myc-ER$^{TAM}$ transgene which enables them to proliferate indefinitely in presence of epidermal growth factor (EGF), basic fibroblast growth factor (bFGF) and 4-hydroxy-tamoxifen (4-OHT) (Pollock, K. et al (2006). Removal of these factors induces spontaneous differentiation into neurons, astrocytes or oligodendrocytes.

Serum Samples

Proliferating and differentiating HPC0A07/03C cells were exposed to 1% human serum from individuals diagnosed with MCI who 1) later developed dementia due to AD (MCI converters, n=38, 2-5 annual follow-up visits) or 2) did not develop AD (MCI non-converters, n=18, 3-6 annual follow-up visits), had transient memory problems but remained cognitively stable over a period of at least 3 years from diagnosis. Longitudinal serum samples from each study participant were used to monitor changes in HN over time. That enabled obtaining a neurogenesis readout corresponding to each follow-up visit and modelling within- and between-subjects variability in HN over time. A minimum of three annual assessments was required when selecting MCI non-converters for the study. Likewise, an absolute minimum were 2 serum samples from MCI converters—one collected at the time of conversion, and at least one serum sample from MCI stage. Serum samples were stored in −80° C. and have undergone one freeze/thaw cycle before performing experiments.

All serum samples were collected within the framework of the EU AddNeuroMed Consortium, a multicenter European study, and King's Health Partners-Dementia Case Register (KHP-DCR), a UK clinic and population based study, in accordance with principles of informed consent (Lovestone, S. et al (2009). The diagnosis of probable AD was made according to (McKhann, G. et al 1984) and [27] criteria. MCI was diagnosed according to (Peterson, R. C. et al 2001) criteria. Clinical diagnosis was confirmed during consecutive follow-up visits. Serum was collected at the time of cognitive assessments.

In vitro Assay to Investigate Impact of the Systemic Environment on Human Hippocampal Neurogenesis To study how the systemic environment (i.e. serum, or more specifically the systemic milieu) influences human HN, we developed and optimized an in vitro assay, in which HPC0A07/03C cells are treated with 1% serum. Serum was added to cell culture during both proliferation (48 hours) and differentiation (7 days). 24 hours after seeding cell medium (for details see Anacker, C. et al 2011) was replaced with medium containing 1% serum. After 48 hours cells were fixed in 4% paraformaldehyde.

In order to investigate systemic effects on differentiation of HPC0A07/03C cells, after 48 hours of proliferation in the presence of 1% serum (as described above), medium was replaced by one without 4-OHT, EGF and FGF to enable cells to spontaneously differentiate. Experiments were terminated after 7 days of differentiation to avoid medium change and another serum supplementation. In addition, this time is sufficient to detect changes in immature and mature neurons counts (Anacker, C. et al 2011; Zunszain, P. A. et al 2012; Anacker, C. et al 2013). Medium supplemented with 1% serum was added only once during both proliferation and differentiation of the HPC0A07/03C cells. For each experiment three biological replicates (cells of three different passage numbers) are used and for each biological replicate there will be technical triplicates. All experiments were performed using the HPC0A07/03C cells of passage number ranging from 15 to 24.

Immunohistochemistry and Semi-Automatic Analysis

Proliferation was assessed using rabbit polyclonal anti-Ki67 (Abcam) antibody; apoptosis—rabbit monoclonal anti-CC3 antibody; neuronal differentiation—rabbit polyclonal anti-Dcx (Abcam), mouse monoclonal anti-Map2 (Abcam). Secondary antibodies were conjugated with Alexa 488 or Alexa 555 (Invitrogen) and nuclei were counterstained with DAPI. Semi-automatic quantification of cell numbers and phenotypes was performed in 96-well plates, using the high-throughput instrument Cellinsight Personal Cell Imager V2 (ThermoFisher Scientific).

Statistical Analysis

For univariate analyses two-tailed paired t-student test, one- and two-way ANOVA with post hoc comparisons using the Bonferroni correction were used.

Due to the longitudinal aspect of the dataset, the inventors used linear mixed-effects regression models for repeated measures as they enable inclusion of varying number of assessment information available for each individual and do not require equal time intervals between the follow-up visits. Random intercept and random slope models were fitted with restricted maximum likelihood as the method of estimation. All analyses were adjusted for the effect of age, gender, and education status.

Each serum donor was assigned an ID in order to specify random effects in the models. The age of the individuals was centred at the cohort median (77 years) to aid interpretation of the models. Time to conversion was measured in years and centred at 0 which indicated conversion from MCI to AD. Time before conversion was assigned negative and time after conversion—positive values. Education was entered in the models either as years of education or it was dichotomized at the median (low ≤10, high >10 years of education). Classification to MCI converters or non-converters was dichotomous (MCI converters were assigned 1, non-converters −0).

Given that many individual characteristics or comorbidities might affect HN and/or AD risk, among the potential predictors considered in the models were: AD risk factors (gender, age centred around median and time to conversion (or time from baseline for MCI non-converters)), education level, solitary living and MMSE score (baseline MMSE, MMSE score change/year); comorbidities (diabetes, arthritis, hypertension, hypothyroidism, depression, cancer, stroke, angina, infections and allergies); drug intake (antidepressants, statins, nonsteroidal anti-inflammatory drugs); dietary supplements (vitamins, omega-3 fatty acids); lifestyle related factors (alcoholism, smoking). In addition, we also tested some biologically plausible interactions of different predictors. All mixed-effects regression models were assessed using Akaike Information Criterion (AIC), likelihood-ratio test and deviance.

Logistic regression and receiver operating characteristic (ROC) curve were carried out to determine the classification accuracy of selected variables in predicting conversion to AD. Area under the curve was used to estimate the discrimination between MCI converters and stable MCI.

All statistical analyses were performed using Prism 5.0 software (GraphPad Software) or STATA 13.

Results

Baseline and Longitudinal Characteristics of Serum Donors

Detailed information about the baseline characteristics and epidemiological history of individuals enrolled in the study is presented in Table 1. The "baseline" refers to the point at which the assay is first performed. This is the first patient visit when serum was collected. All participants were age- (p=0.320) and gender-matched (p=0.129, see Table 1). MCI converters completed significantly less years of education compared with MCI non-converters (p=0.002). They also scored significantly lower in MMSE (p=0.031).

TABLE 1

Baseline characteristics and epidemiological history of the study participants. Comorbidities represent either history of disease or being presently affected. Drug intake means either history of medications or current intake. All data is presented as number (%) or mean (±SD).

| Baseline characteristics | MCI converters | MCI non-converters |
|---|---|---|
| Gender (%, female; F/M) | 60.52% | 38.89% |
| Age at baseline (years ± SD) | 76.02 ± 7.81 | 78.05 ± 5.08 |
| MMSE at baseline (±SD) | 26.78 ± 1.97 | 27.94 ± 1.43 |
| Education (years ± SD) | 8.95 ± 4.53 | 12.83 ± 3.09 |
| Years from baseline until conversion/last assessment (±SD; range) | 2.35 ± 0.79; 2-5.08 | 4.86 ± 1.35; 2.92-7 |
| Comorbidities | | |
| Hypertension | 12 (31.58%) | 10 (55.55%) |
| Heart attack ever | 1 (2.63%) | 4 (22.22%) |
| Angina | 4 (10.53%) | 3 (16.67%) |
| Depression | 20 (52.63%) | 9 (50%) |
| Arthritis | 1 (2.63%) | 3 (16.67%) |
| Asthma | 2 (5.26%) | 1 (5.55%) |
| Cancer | 5 (13.16%) | 6 (33.33%) |
| Glaucoma | 2 (5.26%) | 1 (5.55%) |
| Hypothyroidism | 2 (5.26%) | 3 (16.67%) |
| Infections, allergies | 5 (13.16%) | 2 (11.11%) |
| Stroke/TIA | 4 (10.53%) | 2 (11.11%) |
| Diabetes | 7 (18.42%) | 2 (11.11%) |
| Drug intake | | |
| Antidepressants | 13 (34.21%) | 3 (16.67%) |
| NSAIDs | 1 (2.63%) | 0 (0%) |
| Analgesics | 7 (18.42%) | 5 (27.78%) |
| AD drugs | 11 (28.95%) | 0 (0%) |
| Metformin | 4 (10.53%) | 1 (5.55%) |
| Sleeping pills | 3 (7.89%) | 2 (11.11%) |
| Statins | 15 (39.47%) | 8 (44.44%) |
| Lifestyle factors | | |
| Excessive alcohol intake | 1 (2.63%) | 3 (16.67%) |
| Smoking (ever) | 4 (10.53%) | 7 (38.89%) |
| Solitary living | 16 (42.10%) | 9 (50%) |
| Supplements* intake | 7 (18.42%) | 5 (27.78%) |

*Supplements included vitamins and omega-3 fatty acids.

The epidemiological history of the serum donors was used at the modelling stage, enabling adjustment for any potential confounding factors that might affect HN and/or AD.

Decreased Proliferation and Increased Neurogenesis Characterize Progression from MCI to AD First, using the longitudinal serum samples from the MCI converters the inventors analysed the effect of systemic environment on HN from baseline diagnosis until conversion to AD. They obtained neurogenesis readouts corresponding to each follow-up visit and performed modelling of the intra- and inter-individual differences in the systemic effects on human HN. Mixed-effects models for repeated measures were fitted to identify factors affecting trajectories of HN changes. Since age was not a significant predictor of HN (data not shown), they used another measure enabling longitudinal analysis—time to conversion, i.e. time in years to the clinical diagnosis of dementia due to AD. Because the last serum sample used in the study was obtained at the time of conversion to AD, it is assigned the value of 0, and time before conversion—negative values (i.e. one year before conversion is −1 year).

MCI to AD Converters' Serum Effects on Proliferation of Human Hippocampal Progenitor Cells The model with random intercept predicts that over the disease progression there is an increase in the number of hippocampal progenitor cells (p=0.002, Table 2). This is not related to increased proliferation, as conversely, decreasing level of proliferation (% Ki67+ cells, p<0.0001, Table 2) of hippocampal progenitor cells over time to conversion was detected. Time to conversion was the only significant predictor of proliferation and cell number in both random intercept models (see Table 2) for average cell count and % Ki67+ cells.

In addition, the mixed effects model with a random slope predicts that the level of apoptotic cell death (% CC3+ cells, p<0.0001, Table 2) increases with decreasing time to conversion to AD. For individuals with higher education that increase is smaller as compared to those with less than 10.5 years of education, suggesting that environmental factors related to education level, such as diet, might significantly impact on cell death during disease progression.

The percentage of variance that accounted for the average cell count was 66.9%, 88.92% for Ki67 and 88.3% for CC3, indicating excellent fit of the models.

MCI to AD Converters' Serum Effects on Differentiation of Human Hippocampal Progenitor Cells Human hippocampal progenitor cells were exposed to the serum samples during both proliferation and differentiation. Mixed effects models with random intercept (for cell count, Dcx) or random slope (for Map2) predict that there is an increased cell number (p=0.037, Table 2) and increased level of immature (Dcx, p=0.021, Table 2) and mature (Map2, p=0.044, Table 2) neurons with disease progression. We did not detect significant alterations in the number of apoptotic human hippocampal progenitor cells during differentiation (data not shown).

Time to conversion was the only significant predictor of the average cell number during the differentiation stage of the assay (see Table 2). MMSE score at baseline and time to conversion predicted the number of immature neurons, i.e. the higher MMSE score at baseline, the lower number of Dcx-positive neurons. Gender of the serum donors was significantly influencing the predicted level of mature neurons, with females having on average 3.34% less Map2-positive cells as compared to males, when controlling for the time to conversion.

The percentage of variance that accounted for average cell count was 72.47%, 58.31% for Dcx, 55.83% for Map2, indicating a moderate fit of the models.

Variables such as and comorbidities (as listed in Table 1) were not significant when included in the mixed-effects models with respect to proliferation and differentiation stages of the assay. No significant interaction effects were determined.

TABLE 2

Factors affecting changes in the human hippocampal neurogenesis (dependent variable) when the HPC0A07/03C cells are exposed to 1% serum from the MCI converters. Models with the lowest AIC and deviance were selected as the best fit. Coefficient estimates (β), standard errors SE (β), 95% confidence intervals (CI) around the regression coefficient and significance levels for all predictors in the analysis are provided.

| | | Random intercept (model 0) | | | | Random intercept (model 1) | | | | Random intercept (model 2) | | | | Random slope (model 3) | | | |
|---|---|---|---|---|---|---|---|---|---|---|---|---|---|---|---|---|---|
| Parameter | Significant predictors | β | SE (β) | 95% CI | p | β | SE | 95% CI | p | β | SE | 95% CI | p | β | SE | 95% CI | p |
| PROLIFERATION ASSAY | Average cell count (proliferation) | | | | | | | | | | | | | | | | |
| | β₀ Intercept | 562.25 | 9.14 | 544.35-580.16 | <0.001 | 573.04 | 9.78 | 553.86-592.21 | <0.001 | | | | | | | | |
| | β₁ Time to conversion | — | | | | 15.83 | 5.21 | 5.61-26.03 | 0.002 | | | | | | | | |
| | -log-likelihood | -461.86 | | | | -454.98 | | | | | | | | | | | |
| | p-value for the model | — | | | | 0.002 | | | | | | | | | | | |
| | Deviance | 923.72 | | | | 909.96 | | | | | | | | | | | |
| | AIC | 929.73 | | | | 917.97 | | | | | | | | | | | |
| | Ki67 | | | | | | | | | | | | | | | | |
| | β₀ Intercept | 72.53 | 0.92 | 70.72-74.33 | <0.001 | 71.59 | 0.93 | 69.77-73.42 | <0.001 | | | | | | | | |
| | β₁ Time to conversion | — | | | | -1.39 | 0.29 | -1.95--0.83 | <0.001 | | | | | | | | |
| | -log-likelihood | -242.15 | | | | -232.60 | | | | | | | | | | | |
| | p-value for the model | — | | | | <0.0001 | | | | | | | | | | | |
| | Deviance | 484.3 | | | | 465.2 | | | | | | | | | | | |
| | AIC | 490.31 | | | | 473.20 | | | | | | | | | | | |
| | CC3 | | | | | | | | | | | | | | | | |
| | β₀ Intercept | 2.16 | 0.15 | 1.86-2.45 | <0.001 | 2.24 | 0.15 | 1.94-2.54 | <0.001 | 2.45 | 0.18 | 2.10-2.79 | <0.001 | 2.50 | 0.18 | 2.15-2.86 | <0.001 |
| | β₁ Time to conversion | | | | | 0.12 | 0.05 | 0.02-0.22 | 0.023 | 0.12 | 0.05 | 0.02-0.22 | 0.024 | 0.19 | 0.05 | .089-0.29 | <0.001 |

TABLE 2-continued

Factors affecting changes in the human hippocampal neurogenesis (dependent variable) when the HPC0A07/03C cells are exposed to 1% serum from the MCI converters. Models with the lowest AIC and deviance were selected as the best fit. Coefficient estimates (β), standard errors SE (β), 95% confidence intervals (CI) around the regression coefficient and significance levels for all predictors in the analysis are provided.

| Parameter | Significant predictors | Random intercept (model 0) | | | | Random intercept (model 1) | | | | Random intercept (model 2) | | | | Random slope (model 3) | | | |
|---|---|---|---|---|---|---|---|---|---|---|---|---|---|---|---|---|---|
| | | β | SE (β) | 95% CI | p | β | SE | 95% CI | p | β | SE | 95% CI | p | β | SE | 95% CI | p |
| $\beta_2$ | >=10 years of education | | | | | | | | | -.60 | 0.30 | -1.19--0.02 | 0.042 | -0.70 | 0.26 | -1.21--0.19 | 0.007 |
| -log-likelihood | | | | -86.71 | | | -86.19 | | | | -84.48 | | | | -81.66 | | |
| p-value for the model | | | | — | | | 0.023 | | | | 0.009 | | | | <0.0001 | | |
| Deviance | | | | 173.42 | | | 172.38 | | | | 168.96 | | | | 177.31 | | |
| AIC | | | | 179.42 | | | 180.38 | | | | 178.97 | | | | | | |
| Average cell count (differentiation) | | | | | | | | | | | | | | | | | |
| $\beta_0$ | Intercept | 647.56 | 10.68 | 626.63-668.49 | <0.001 | 654.58 | 10.92 | 633.18-675.99 | <0.001 | 891.63 | 96.61 | 702.29-1080.98 | <0.001 | | | | |
| $\beta_1$ | Time to conversion | | | — | | 10.43 | 5.00 | 0.62-20.24 | 0.037 | 10.25 | 5.00 | 0.44-20.06 | 0.041 | | | | |
| $\beta_2$ | Age at baseline | | | | | | | | | -3.12 | 1.26 | -5.60--0.64 | 0.014 | | | | |
| p-value for the model | | — | | | | 0.037 | | | | 0.005 | | | | | | | |
| -log-likelihood | | -462.24 | | | | -457.57 | | | | -453.54 | | | | | | | |
| Deviance | | 924.48 | | | | 915.14 | | | | 907.08 | | | | | | | |
| AIC | | 930.47 | | | | 923.14 | | | | 917.10 | | | | | | | |
| Dcx | | | | | | | | | | | | | | | | | |
| $\beta_0$ | Intercept | 15.02 | 0.77 | 13.52-16.53 | <0.001 | 15.73 | 0.81 | 14.14-17.32 | <0.001 | 42.76 | 9.55 | 24.04-61.49 | <0.001 | | | | |
| $\beta_1$ | Time to conversion | | | | | 1.04 | 0.45 | 0.15-1.92 | 0.021 | 1.00 | 0.46 | 0.08-1.91 | 0.032 | | | | |

TABLE 2-continued

Factors affecting changes in the human hippocampal neurogenesis (dependent variable) when the HPC0A07/03C cells are exposed to 1% serum from the MCI converters. Models with the lowest AIC and deviance were selected as the best fit. Coefficient estimates (β), standard errors SE (β), 95% confidence intervals (CI) around the regression coefficient and significance levels for all predictors in the analysis are provided.

| Parameter | Significant predictors | Random intercept (model 0) | | | | Random intercept (model 1) | | | | Random intercept (model 2) | | | | Random slope (model 3) | | | |
|---|---|---|---|---|---|---|---|---|---|---|---|---|---|---|---|---|---|
| | | β | SE (β) | 95% CI | p | β | SE | 95% CI | p | β | SE | 95% CI | p | β | SE | 95% CI | p |
| $\beta_2$ | MMSE at baseline | — | | | | 0.021 | | | | -1.01 | 0.35 | -1.70--0.31 | 0.005 | | | | |
| p-value for the model | | | | | | | | | | 0.001 | | | | | | | |
| -log-likelihood | | -250.51 | | | | -247.80 | | | | -241.84 | | | | | | | |
| Deviance | | 501.02 | | | | 495.6 | | | | 483.68 | | | | | | | |
| AIC | | 507.03 | | | | 503.59 | | | | 493.68 | | | | | | | |
| Map2 | | | | | | | | | | | | | | | | | |
| $\beta_0$ | Intercept | 16.06 | 0.68 | 14.73-17.39 | <0.001 | 16.63 | 0.72 | 15.22-18.05 | <0.001 | 18.67 | 1.02 | 16.67-20.66 | <0.001 | | | | |
| $\beta_1$ | Time to conversion | | | | | 0.84 | 0.42 | 0.02-1.66 | 0.044 | 0.86 | 0.42 | 0.04-1.68 | 0.039 | | | | |
| $\beta_2$ | Female | | | | | | | | | -3.34 | 1.25 | -5.80--0.88 | 0.008 | | | | |
| p-value for the model | | — | | | | 0.044 | | | | 0.003 | | | | | | | |
| -log-likelihood | | -241.76 | | | | -239.71 | | | | -235.26 | | | | | | | |
| Deviance | | 483.52 | | | | 479.42 | | | | 470.52 | | | | | | | |
| AIC | | 489.52 | | | | 487.42 | | | | 480.52 | | | | | | | |

TABLE 3

Significant factors affecting human hippocampal neurogenesis (dependent variable) when the HPC0A07/03C cells are exposed to 1% serum from either MCI converters or MCI non-converters. Models with the lowest AIC and deviance were selected as the best fit. Coefficient estimates ($\beta$), standard errors SE ($\beta$), 95% confidence intervals (CI) around the regression coefficient and significance levels for all predictors in the analysis are provided.

| Parameter | Significant predictor | Random intercept (model 0) | | | | Random intercept (model 1) | | | |
|---|---|---|---|---|---|---|---|---|---|
| | | $\beta$ | SE ($\beta$) | 95% CI | p | $\beta$ | SE ($\beta$) | 95% CI | p |
| Average cell number (proliferation) | | | | | | | | | |
| $\beta_0$ | Intercept | 530.783 | 10.93 | 509.36-552.20 | <0.001 | 498.54 | 16.67 | 465.86-531.22 | <0.001 |
| $\beta_1$ | conversion | | | | | 74.79 | 19.83 | 35.92-113.65 | <0.001 |
| $\beta_2$ | Time to conversion/last visit | | | | | 17.08 | 2.71 | 11.75-22.40 | <0.001 |
| p-value for the model | | | | | | <0.0001 | | | |
| −log-likelihood | | −900.10 | | | | −867.74 | | | |
| Deviance | | 1800.2 | | | | 1735.48 | | | |
| AIC | | 1806.21 | | | | 1745.49 | | | |
| Average cell number (differentiation) | | | | | | | | | |
| $\beta_0$ | Intercept | 658.5991 | 9.13 | 640.70-676.50 | <0.001 | 701.94 | 16.06 | 670.46-733.41 | <0.001 |
| $\beta_1$ | conversion | | | | | −47.64 | 18.98 | −84.83-−10.44 | 0.012 |
| $\beta_2$ | Time to conversion/last visit | | | | | 11.48 | 2.95 | 5.69-17.27 | <0.001 |
| p-value for the model | | | | | | 0.0001 | | | |
| −log-likelihood | | −889.37 | | | | −874.64 | | | |
| Deviance | | 1778.74 | | | | 1749.28 | | | |
| AIC | | 1784.73 | | | | 1759.28 | | | |
| % Map2 | | | | | | | | | |
| $\beta_0$ | Intercept | 14.82 | 0.60 | 13.65-15.99 | <0.001 | 13.45 | 1.02 | 11.46-15.44 | <0.001 |
| $\beta_1$ | conversion | | | | | 2.96 | 1.19 | 0.64-5.29 | 0.012 |
| $\beta_2$ | Time to conversion/last visit | | | | | 0.56 | 0.23 | 0.12-1.01 | 0.014 |

TABLE 3-continued

Significant factors affecting human hippocampal neurogenesis (dependent variable) when the HPC0A07/03C cells are exposed to 1% serum from either MCI converters or MCI non-converters. Models with the lowest AIC and deviance were selected as the best fit. Coefficient estimates (β), standard errors SE (β), 95% confidence intervals (CI) around the regression coefficient and significance levels for all predictors in the analysis are provided.

| | | | | | | |
|---|---|---|---|---|---|---|
| p-value for the model | — | | 0.0005 | | | |
| −log-likelihood | −457.37 | | −449.54 | | | |
| Deviance | 914.74 | | 899.08 | | | |
| AIC | 920.73 | | 909.08 | | | |

| | | Random slope (model 2) | | | |
|---|---|---|---|---|---|
| Parameter | Significant predictor | β | SE (β) | 95% CI | p |
| Average cell number (proliferation) | | | | | |
| $\beta_0$ | Intercept | 499.05 | 15.95 | 467.80-530.31 | <0.001 |
| $\beta_1$ | conversion | 74.90 | 19.16 | 37.35-112.44 | <0.001 |
| $\beta_2$ | Time to conversion/ last visit | 18.24 | 3.91 | 10.59-25.90 | <0.001 |
| p-value for the model | | <0.0001 | | | |
| −log-likelihood | | −864.25 | | | |
| Deviance | | 1728.5 | | | |
| AIC | | 1740.49 | | | |
| Average cell number (differentiation) | | | | | |
| $\beta_0$ | Intercept | | | | |
| $\beta_1$ | conversion | | | | |
| $\beta_2$ | Time to conversion/ last visit | | | | |
| p-value for the model | | | | | |
| −log-likelihood | | | | | |
| Deviance | | | | | |
| AIC | | | | | |
| % Map2 | | | | | |
| $\beta_0$ | Intercept | | | | |
| $\beta_1$ | conversion | | | | |
| $\beta_2$ | Time to conversion/ last visit | | | | |
| p-value for the model | | | | | |
| −log-likelihood | | | | | |
| Deviance | | | | | |
| AIC | | | | | |

MCI Converters vs MCI Non-Converters

Comparison of the effects of serum from MCI converters and MCI non-converters on HN demonstrated significant differences during both proliferation and differentiation of human hippocampal progenitor cells.

Figure 1:
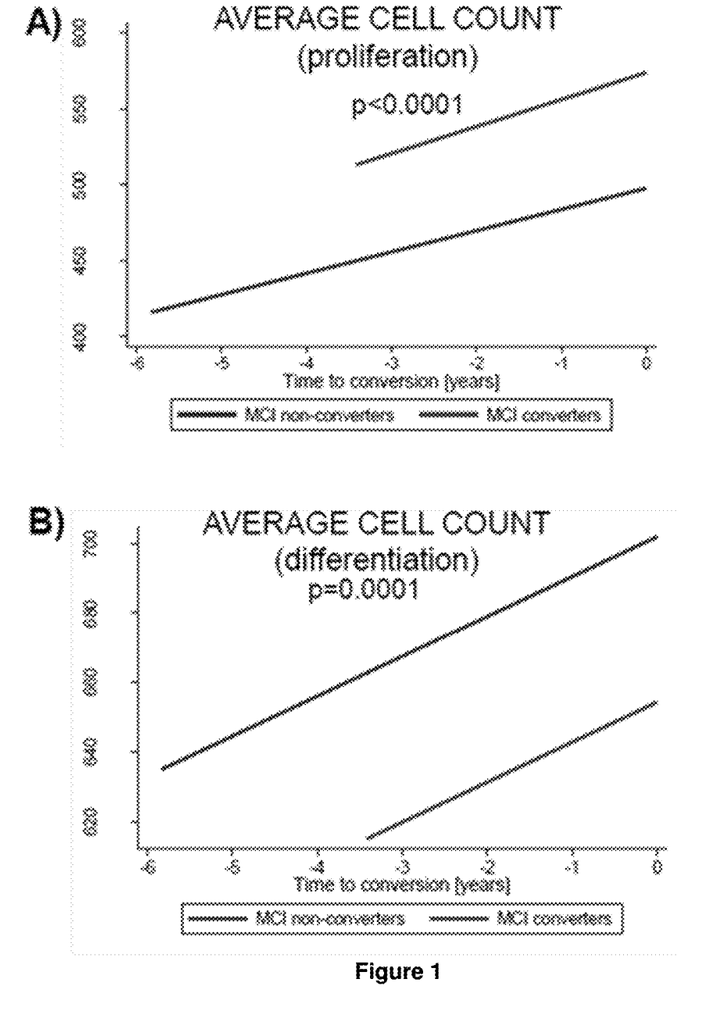
FIG. 1 shows the effect of serum from MCI converters and MCI non-converters during the proliferation (A, C, E) and differentiation (B, D, F) phases of in vitro hippocampal neurogenesis. (C) Shows the change in number of proliferating cells ($Ki67^+$ cells) when hippocampal progenitor cells are treated with 1% serum from MCI converters and MCI non-converters. (D) Shows the percentage of mature $Map2^+$ neurons that result from neurogenesis when hippocampal progenitor cells are cultured in the presence of serum from either MCI converters or MCI non-converters during proliferation and subsequent differentiation stages of the assay. (E, F) shows that serum from MCI converters triggers decreased survival of proliferating (E) and differentiating (F) hippocampal progenitor cells and this effect is time independent. On the x-axis of A to D the point of conversion to AD is labelled at 0, whereas 0 for MCI non-converters represents the last visit.

Using fitted models the inventors demonstrated that during the proliferation stage of the assay the number of hippocampal progenitor cells exposed to serum increases with consecutive follow-up visits, however the number of cells treated with serum from MCI converters is higher as compared to the effect of serum from MCI non-converters (p<0.0001 FIG. 1).

On the other hand, it was observed that the number of Ki67-positive cells decreases with time, however significantly less so when they are subjected to serum from MCI converters (p=0.0001, FIG. 1c). In addition, it was detected that serum from MCI converters leads to higher apoptotic cell death during both proliferation (p=0.0001, $R^2$=0.099, Adj $R^2$=0.093 FIG. 1e) and differentiation (p<0.0001, $R^2$=0.263, Adj $R^2$=0.258, FIG. 1f), however, this effect is time-independent.

Fitted models indicated that during the differentiation stage of the assay there is an overall decrease in the number of cells treated with serum, and human hippocampal progenitor cells treated with serum from MCI converters were characterized by significantly higher drop in number as compared to cells treated with serum from MCI non-converters (p=0.0001). Moreover, the number of mature neurons (Map2-positive cells) significantly increased when cells were treated with serum from MCI converters (p=0.0005 FIG. 1d).

By applying stepwise logistic regression to the baseline data, the inventors determined the best predictors of conversion from MCI to AD.

Table 4 shows predictors of conversion to AD, based on the in vitro model of human hippocampal neurogenesis and stepwise logistic regression analysis. (Predictors: Education (measured in years), average cell count during proliferation, proliferation marker (Ki67), apoptosis during differentiation (cleaved caspase 3 (CC3)).

TABLE 5

|  | Odds Ratio | P > z* |
| --- | --- | --- |
| Education (years) | 0.72 | 0.040 |
| Average cell count (proliferation) | 1.03 | 0.001 |
| Ki67 (proliferation) | 1.35 | 0.038 |
| CC3 (differentiation) | 3.49 | 0.016 |
| Intercept | 1.68e−15 | 0.012 |

*p-value for each of the predictors in the model

Figure 2:
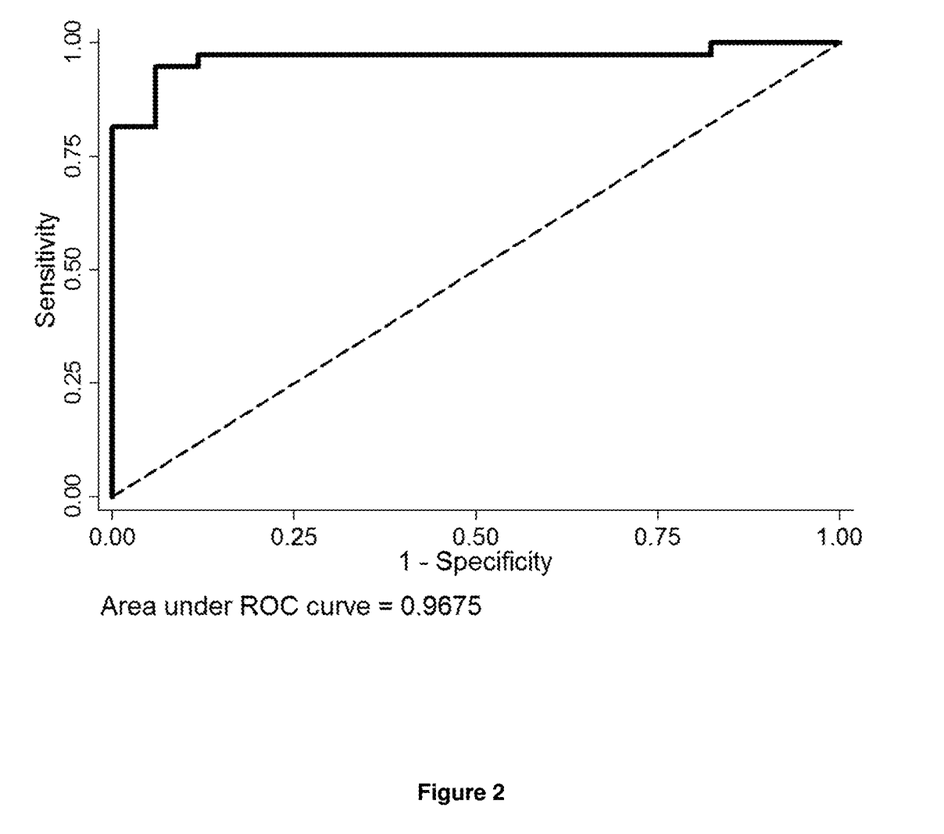
FIG. 2 shows the Receiver Operator Characteristic (ROC) curve demonstrating prediction accuracy of statistical model estimating likelihood of conversion to Alzheimer's disease. The prediction model (AUC=0.9675) indicates an excellent discriminative performance of the model. Sensitivity=92.11%, Specificity=94.12%, Positive predictive value=97.22%, Negative predictive value=84.21%.

The fit of the model was confirmed using Hosmer-Lemeshow goodness of fit (p=0.324) and Stata linktest, demonstrating no specification errors (_hat=0.001, _hatsq=0.110). To assess the accuracy of the selected predictors in assigning individuals into MCI converters or non-converters groups, receiver operating characteristic (ROC) analysis was performed (see FIG. 2). FIG. 2 demonstrates excellent discriminatory power (area under the curve, AUC=96.75%) of the model to distinguish between future converters and non-converters. It shows that the model correctly classifies 92.11% converters and 94.12% MCI non-converters are correctly discriminated.

CONCLUSION

This data demonstrates that incubating a serum sample obtained from a patient diagnosed with MCI with hippocampal progenitor cells in vitro, and subsequently monitoring the effect of the serum sample on in vitro hippocampal neurogenesis, can be used to accurately predict the likelihood that said patient will convert from MCI to Alzheimer's disease.

The invention claimed is:

1. An in vitro cell-based assay method comprising the steps of:
   (a) culturing conditionally immortalized human hippocampal progenitor cells in a culture medium comprising serum during a period of proliferation of said progenitor cells, the serum obtained from a patient who has received a diagnosis of mild cognitive impairment (MCI);
   (b) subsequently culturing said conditionally immortalized hippocampal progenitor cells in a culture medium comprising the serum obtained from said patient, during a period of differentiation of said progenitor cells;
   (c) measuring the level of proliferation of said cultured progenitor cells, wherein one or more cellular markers that increase during proliferation are measured:
   (d) measuring the average cell count of said cultured progenitor cells during or after the period of proliferation; and
   (e) measuring apoptotic cell death after differentiation of the proliferated hippocampal progenitor cells, wherein one or more apoptotic-associated proteins are measured, wherein the outcomes of each of (c) to (e) result in a probability score, the result of which indicates the likelihood of the patient with mild cognitive impairment (MCI) converting to Alzheimer's disease (AD).

2. The assay of claim 1, wherein the final concentration of the serum in the culture medium in (a) and (b) is from 0.5% to 5%.

3. The assay of claim 1, wherein step (a) comprises adding the serum to the culture medium 24 hours after seeding the cells in the culture medium.

4. The assay of claim 1, wherein the culture medium in step (a) comprises epidermal growth factor, basic fibroblast growth factor and 4-hydroxytestosterone.

5. The assay of claim 1, wherein the period of proliferation referred to in step (a) is a 48 hour period.

6. The assay of claim 1, wherein the culture medium is changed between steps (a) and (b), and wherein the culture medium used in (b) does not comprise epidermal growth factor, basic fibroblast growth factor, and 4-hyxdroxytestosterone.

7. The assay of claim 6, wherein the serum is added to the culture medium at the beginning of the differentiation period of step (b).

8. The assay of claim 1, wherein the period of differentiation referred to in step (b) is a period of up to 7 days.

9. The assay of claim 1, comprising a further step of determining the education status of the patient.

10. The assay of claim 9, wherein the education status of the patient is included in the probability score.

11. The assay of claim 1, wherein education status corresponds to the total number of years of formal education.

12. The assay of claim 1, wherein the hippocampal progenitor cells are human multipotent hippocampal progenitor cells.

13. The assay of claim 1, wherein the hippocampal progenitor cells are cells from the HPCOA07/03C cell line.

14. The assay of claim 1, wherein the level of proliferation of the hippocampal progenitor cells is determined at the end of the proliferation period.

15. The assay of claim 14, wherein the level of proliferation is determined by measuring Ki67 expression of the hippocampal cells.

16. The assay of claim 15, wherein Ki67 expression is measured using an anti-Ki67 antibody.

17. The assay of claim 1, wherein the average cell count is determined at the end of the proliferation period and at the end of the differentiation period.

18. The assay of claim 1, wherein apoptotic cell death is determined at the end of the differentiation period.

19. The assay of claim 1, wherein apoptotic cell death is determined by measuring cleaved caspase 3 expression.

* * * * *